United States Patent [19]

Lutz

[11] 4,284,837

[45] Aug. 18, 1981

[54] PROCESS FOR RECOVERY OF AN ALIPHATIC DIOL OLIGOMERIZATION SOLVENT

[75] Inventor: Eugene F. Lutz, Houston, Tex.

[73] Assignee: Shell Oil Company, Houston, Tex.

[21] Appl. No.: 144,805

[22] Filed: Apr. 29, 1980

[51] Int. Cl.$^3$ .............................................. C07C 2/02
[52] U.S. Cl. .................................... 585/523; 585/520; 585/525; 203/6
[58] Field of Search ...................... 585/520, 523, 525; 203/6

[56] References Cited

U.S. PATENT DOCUMENTS

| | | | |
|---|---|---|---|
| 3,644,564 | 2/1972 | van Zwet et al. | 585/520 |
| 3,647,914 | 3/1972 | Glockner et al. | 585/520 |
| 3,647,915 | 3/1972 | Bauer et al. | 585/523 |
| 3,676,523 | 7/1972 | Mason | 585/523 |
| 3,686,351 | 8/1972 | Mason | 585/523 |
| 3,737,475 | 6/1973 | Mason | 585/523 |
| 3,825,615 | 7/1974 | Lutz | 585/523 |
| 4,020,121 | 4/1977 | Kister et al. | 585/520 |

*Primary Examiner*—Curtis R. Davis

[57] ABSTRACT

An improved technique is described for the recovery of aliphatic diol reaction solvent in a process wherein ethylene is oligomerized at elevated temperature and pressure by contact with a solution of a nickel complex catalyst in an aliphatic diol solvent to afford a reaction product made up of (a) a liquid solvent phase containing dissolved catalyst, (b) a liquid hydrocarbon phase comprising ethylene oligomers containing dissolved ethylene, catalyst and diol solvent and (c) gaseous ethylene, said reaction product being passed to a series of phase separation zones whereby gaseous ethylene and a substantial portion of the diol reaction solvent containing dissolved catalyst are separated and recycled to the oligomerization reaction zone with a minor portion of the separated reaction solvent being passed to a fractionation zone for removal of light ends and spent catalyst prior to reuse in the process. With this improved process, the formation of diol solvent degradation products, e.g., acetals and hemiacetals, are substantially avoided in the diol solvent fractionation step by adding a minor amount of an alkali metal hydroxide to the fractionation zone.

8 Claims, No Drawings

PROCESS FOR RECOVERY OF AN ALIPHATIC DIOL OLIGOMERIZATION SOLVENT

BACKGROUND OF THE INVENTION

This invention relates to an improved process for the production of linear alpha-olefins by oligomerization of ethylene. More particularly, this invention is directed to an improvement in the recovery of diol reaction solvent in a process wherein ethylene is oligomerized by contact with a catalytic nickel complex dissolved in an aliphatic diol reaction solvent.

Linear monoolefins are compounds of established utility in a variety of applications. Terminal linear monoolefins, particularly those having 12 to 20 carbon atoms per molecule, are known to be useful as intermediates in the production of various types of detergents, e.g., alcohols, ethoxylates, etc.

Several synthetic techniques have been developed for the preparation of terminal linear monoolefins in the detergent range. One very attractive synthetic method from the standpoint of raw material availability and cost involves oligomerization of ethylene to higher molecular weight linear monoolefins (even numbered alpha-monoolefins) by contact with a catalytically active nickel complex dissolved in certain polar solvents. One class of suitable nickel complex catalysts for ethylene oligomerization is prepared as the reaction product of an olefinic nickel compound, including zero-valent nickel compounds such as bis(cyclooctadiene) nickel (O) or π-allyl nickel compounds, and a suitable bidentate ligand as described in U.S. Pat. No. 3,644,564 to Van Zwet et al, U.S. Pat. No. 3,647,914 to Glockner et al and U.S. Pat. No. 3,647,915 to Bauer et al. A different and preferred class of nickel complex catalysts can be prepared by contacting in certain polar organic solvents in the presence of ethylene (1) a simple divalent nickel salt which is at least somewhat soluble in the solvent, (2) a boron hydride reducing agent and (3) a suitable bidentate ligand. The preparation of catalysts in this preferred class and their use in ethylene oligomerization are described in U.S. Pat. Nos. 3,676,523, 3,686,351 and 3,737,475 to R. F. Mason and U.S. Pat. No. 3,825,615 to Lutz.

In cases where the oligomerization is carried out using the preferred nickel complex catalysts in a polar organic solvent, preferably an aliphatic diol, the reaction product typically consists of three phases: (1) a liquid solvent phase in which catalysts are dissolved; (2) a liquid hydrocarbon phase which consists of the total oligomer and includes dissolved ethylene, solvent and nickel complex catalyst and (3) gaseous ethylene. In early attempts to recover the oligomer product from this three-phase reaction product by a series of phase separations and flashing or distillation steps, it was discovered that the small amounts of residual catalyst present in the liquid hydrocarbon phase promoted the formation of objectionable, polymeric polyethylene when catalyst, solvent and ethylene are present in the hydrocarbon product phase at conditions under which part of the hydrocarbon phase is removed by flashing or distillation. As one means of preventing the formation of polyethylene, U.S. Pat. No. 4,020,121 to Kister and Lutz discloses a stepwise process for recovery of active catalyst, polar reaction solvent, gaseous ethylene and ethylene oligomers from the oligomerization reaction product in which the liquid hydrocarbon product phase is subject to a scrubbing step using additional polar organic reaction solvent prior to the time that the catalyst-contaminated hydrocarbon phase is subjected to depressurization for removal of ethylene. In general terms, the overall recovery process described in the aforementioned U.S. Pat. No. 4,020,121 includes an initial degassing step wherein entrained ethylene gas is separated from the two liquid components of the oligomerization reaction mixture for direct recycle to the oligomerization zone followed by phase separation of at least part of the solvent phase from the degassed liquid to afford a liquid hydrocarbon phase substantially free of solvent. According to the patent teaching, the separated liquid hydrocarbon product phase is subsequently passed to a product scrubber where it is contacted with a stream of pure oligomerization reaction solvent under sufficient pressure to avoid flashing of dissolved ethylene, said solvent serving to remove residual active catalyst from the hydrocarbon phase. After removal of the residual active catalyst, the separated hydrocarbon product is passed to a deethenizer for removal of dissolved ethylene and the deethenized product is water-scrubbed to remove residual, dissolved or entrained solvent thereby affording an oligomer product essentially free of solvent, catalyst and ethylene. In the process scheme described in this reference, the bulk of the polar reaction solvent phase containing active catalyst from the liquid-liquid phase separation is suitably recycled to the oligomerization zone with the remainder of the separated solvent being passed to a solvent recovery zone in which purified solvent is produced. This solvent recovery zone is suitably comprised of a fractionation column in which light end impurities and spent catalyst are removed thereby affording a purified reaction solvent which is advantageously employed to scrub catalyst residue from the hydrocarbon phase in the product scrubber (see above) or as a solvent source in the preparation of additional catalyst.

While the processing scheme described in the aforementioned U.S. Pat. No. 4,020,121 provides an attractive means of recovering ethylene oligomers from oligomerization reactions employing nickel complex catalysts in polar organic solvents, it is not completely free of problems. One area of difficulty involves the solvent recovery zone wherein reaction solvent is separated from light end impurities and spent catalyst. In particular, it has been found that when aliphatic diols are employed as the source of polar organic solvent in the oligomerization reaction, the conditions required to separate solvent from the spent catalyst in the solvent recovery zone also promote conversion of the diol solvent into a series of oxygenated degradation products. These oxygenated contaminants which are typically oxidized and/or condensed derivatives of the diol solvent (carbonyl compounds, acetals and hemiacetals) have boiling points and solubilities sufficiently similar to the produced oligomers that they are very difficult to remove from the oligomer product if the recovered solvent is recycled to the oligomerization process. For example, when a preferred oligomerization solvent such as 1,4-butanediol is employed, a series of tetrahydrofuran-type impurities are formed in the solvent recovery zone which have solubilities and boiling points quite similar to the oligomer product. Thus, unless these oxygenated impurities are somehow removed or the recovered solvent is not revised in the process, the impurities will appear as contaminants in the final oligomer product in cases where the oligomers are recovered directly or, they may act as catalyst poisons in cases where the oligomer product, or a portion thereof, is subject to further processing such as sequential isomerization and disproportionation described in U.S. Pat. No. 3,766,939 to Berger.

From the foregoing, it is apparent that an advantage could be obtained if the oligomerization solvent recovery could be somehow modified to substantially eliminate the diol solvent degradation products as a source of oligomer product contamination. Further, it would be particularly desirable if the formation of diol solvent degradation products in the solvent recovery zone could be avoided or minimized with minimal process expense and equipment modification.

SUMMARY OF THE INVENTION

An effective and economical means has now been found to avoid or minimize the formation of oxygenated diol solvent degradation products when the diol reaction solvent containing dissolved oligomerization catalyst is recovered by fractionation in accordance with the process scheme disclosed in the aforementioned U.S. Pat. No. 4,020,121 to Kister and Lutz. In particular, it has been discovered that the addition of a minor amount of an alkali metal hydroxide to the fractionation zone wherein diol solvent is being separated from the oligomerization catalyst will substantially reduce or minimize the quantity of oxygenated degradation products which would otherwise be produced by such thermal treatment of the catalyst-containing reaction solvent.

Accordingly, the present invention provides an improved process for the recovery of aliphatic diol reaction solvent in the processing scheme wherein ethylene is oligomerized at elevated temperature and pressure by contact with a solution of a nickel complex catalyst in an aliphatic diol solvent to afford a reaction product made up of (a) a liquid solvent phase containing dissolved catalyst, (b) a liquid hydrocarbon phase comprising ethylene oligomers containing dissolved ethylene, catalyst and diol solvent and (c) gaseous ethylene, said reaction product being passed to a series of phase separation zones whereby gaseous ethylene and a substantial portion of the diol reaction solvent containing dissolved catalyst are separated and recycled to the oligomerization reaction zone with a minor portion of the separated reaction solvent being passed to a fractionation zone for removal of light ends and spent catalyst, prior to its recycle to the oligomerization process; said improved process being characterized by the improvement which comprises contacting the catalyst-containing diol solvent in the fractionation zone with a minor amount of an alkali metal hydroxide. With small amounts of added alkali metal hydroxide, e.g., 2 moles of alkali metal hydroxide per mole of nickel metal in the spent catalyst, it is possible to achieve greater than a 90% w reduction in the quantity of oxygenated diol solvent degradation products, which would otherwise be formed in the solvent recovery step, in extended thermal aging.

DESCRIPTION OF THE PREFERRED EMBODIMENTS

The improved process of the invention is applicable to any processing scheme wherein ethylene is oligomerized by contact with a catalytic nickel complex dissolved in an aliphatic diol solvent and the reaction product is processed to yield a solvent phase contaminated with catalyst which is subsequently distilled to recover catalyst-free solvent. In this regard, the improvement according to the invention is most suitably employed in conjunction with the oligomer recovery process disclosed in U.S. Pat. No. 4,020,121 to Kister et al as modified by subsequent improvements. As noted previously, U.S. Pat. No. 4,020,121 teaches a stepwise oligomer recovery process which substantially eliminates the formation of unwanted, by-product polyethylene during product recovery phase through the removal of trace amounts of active catalyst from the liquid hydrocarbon product phase by means of a polar (diol) reaction solvent wash prior to the time that the catalyst-contaminated hydrocarbon phase is subjected to depressurization for removal of ethylene. The disclosure of U.S. Pat. No. 4,020,121 with respect to the sequence of processing steps and associated process conditions employed to oligomerize ethylene into a range of linear alpha olefins (oligomers) and to recover the oligomer product and reaction solvent from the three phase oligomerization reaction product is herewith incorporated by reference.

In basic terms, the process of U.S. Pat. No. 4,020,121 provides for the recovery of oligomer product from the three phase oligomerization reaction effluent made up of (1) a liquid diol solvent phase containing dissolved nickel complex catalyst, (2) a liquid hydrocarbon phase which consists of total oligomer and includes dissolved ethylene, solvent and nickel complex catalyst and (3) gaseous ethylene by (a) feeding the reaction effluent to a gas-liquid separation zone wherein gaseous ethylene is separated from the liquid product at temperatures and pressures approximating the reaction zone conditions; (b) passing the separated liquid product comprising the liquid solvent phase and hydrocarbon phase to one or more liquid-liquid separation zones in which a substantial portion of liquid diol solvent and catalyst complex are removed to afford a liquid hydrocarbon product phase containing dissolved ethylene and a small amount of solvent and catalyst complex; (c) scrubbing the phase separated liquid hydrocarbon product with purified or fresh diol reaction solvent under sufficient pressure to avoid flashing of dissolved ethylene, said solvent serving to remove residual active catalyst from the hydrocarbon phase; (d) passing the catalyst-free, hydrocarbon product to a deethanizer wherein dissolved ethylene is flashed off at reduced pressure to afford a deethenized hydrocarbon product containing minor amounts of diol solvent; and (e) washing the deethenized product with water to remove residual diol solvent thereby affording a liquid oligomer product essentially free of solvent, catalyst and ethylene. In this process configuration, the separated ethylene gas and a substantial portion of the solvent phase containing active catalyst are suitably recycled to the oligomerization reaction zone with the remainder of the separated solvent being passed to a solvent recovery zone in which purified solvent is produced. It is in this aspect of solvent purification in the process of U.S. Pat. No. 4,020,121, that the process of the present invention is advantageously applied. Preferably, the process of the aforementioned U.S. Pat. No. 4,020,121 is modified to include the aqueous acid hydrolysis and extraction procedure described in U.S. patent application Ser. No. 50,904 filed June 21, 1979, now U.S. Pat. No. 4,229,607 (common assignee). This patent application which is also herewith incorporated by reference, discloses a process improvement whereby the water-washed oligomer product from step (e) above is contacted with an aqueous acid (pH below about 5) at elevated temperatures thereby hydrolyzing and extracting, i.e., removing, any diol solvent decomposition products which form in the oligomerization and recovery process and carry through into the oligomer product.

The improvement according to the invention can be used to advantage with any oligomerization reaction system which employs the nickel complex catalysts described in the "Background of the Invention" in an aliphatic diol solvent and all or a portion of the solvent is recovered from the spent catalyst by distillation, i.e., the catalyst-containing solvent is subject to elevated temperatures for significant time periods. Preferably, the ethylene oligomerization is carried out using a nickel complex catalyst prepared by reacting a bidentate chelating ligand with a simple divalent nickel salt and boron hydride reducing agent in the presence of ethylene in an aliphatic diol solvent. Preparation and use of catalysts of this type are described in U.S. Pat. Nos. 3,676,523, 3,686,351, and 3,737,475 all to R. F. Mason and 3,825,615 to Lutz. In accordance with these patent disclosures, it is preferred to form the nickel complex catalyst with bidentate chelating ligands having a tertiary organophosphorus moiety with a suitable functional group substituted on a carbon atom attached directly to or separated by no more than two carbon atoms from the phosphorus atom of the organophosphorus moiety. Particularly preferred complexes are those described in U.S. Pat. No. 3,676,523 in which the ligand is an o-dihydrocarbyl-phosphinobenzoic acid or its alkali metal salt and most preferably o-diphenylphosphinobenzoic acid; in another preferred complex, described in U.S. Pat. No. 3,825,615, the ligand is dicyclohexyl phosphinopropionic acid or its alkali metal salt. The aforementioned U.S. patents indicate that the catalyst composition is suitably preformed outside the oligomerization reaction zone by mixing together the various ingredients—i.e., the nickel salt, the bidenate ligand and the boron hydride reducing agent—in the presence of ethylene and in the diol solvent; after which the preformed catalyst in diol solvent is added to the reaction zone. However, according to a more recent disclosure, that is U.S. patent application Ser. No. 116,681, filed Jan. 30, 1980 (common assignee) it is advantageous to carry out the oligomerization using the same basic catalyst components by combining in the oligomerization reaction zone (a) a stable preformed complex of nickel, ethylene and boron hydride in a diol solvent, said complex being prepared by contacting in a diol solvent and in the presence of ethylene, (1) a simple divalent nickel salt, (2) a base and (3) a boron hydride transfer agent and (b) a suitable bidentate ligand; the stable preformed complex of nickel in diol solvent and the bidentate ligand being added in separate portions to the reaction zone. Accordingly in a most preferred embodiment, the improvement according to the invention is applied to an oligomerization reaction carried out according to the teachings of the aforementioned U.S. application Ser. No. 116,687 and subsequent product and solvent recovery scheme carried out according to the disclosure of U.S. Pat. No. 4,020,121 as modified by the teaching of U.S. application Ser. No. 50,904, discussed above. For this most preferred embodiment, the disclosure of U.S. application Ser. No. 116,687 is herewith incorporated by reference.

The components used to make up the oligomerization catalysts in the preferred or most preferred modes for carrying out the improvement according to the invention are essentially identical to the components described in the referenced patents and patent application. In particular, in addition to the bidentate ligand compositions described above, the nickel salt employed to make up the stable nickel complex catalyst precursor described in the referenced patent application and the oligomerization catalysts of the referenced patents is suitably any simple divalent nickel salt which is sufficiently soluble in the diol solvent to provide a catalytically effective concentration of nickel complex catalyst. By the terms "simple divalent" nickel salt is meant a nickel atom having a formal valence of +2 and bonded through ionic or electrovalent linkages to two singly charged anionic groups (e.g., halides) or to one doubly charged anionic group (e.g., carbonate) and not complexed with or coordinated to any other additional molecular or ionic species with the exception of water of hydration. Simple divalent nickel salts therefore do not encompass complex divalent nickel salts which are bonded to one or two anionic groups and additionally complexed or coordinated to neutral chelating ligands or groups such as carbon monoxide and phosphines. However, simple divalent nickel salts are meant to include nickel salts containing water of hydration in addition to one or two anionic groups. Suitably, the simple divalent nickel salt employed to prepare the catalyst precursor and oligomerization catalyst will have a solubility of at least 0.0005 mole per liter (0.0005 M) in the diol solvent. A solubility in the diol solvent used to prepare the nickel catalyst precursor is preferably at least 0.001 mole of nickel salt per liter (0.001M) and most preferably at least 0.005 mole of nickel salt per liter of diol solvent (0.005M). In this regard, suitable divalent nickel salts include inorganic nickel salts as well as organic divalent nickel salts. Illustrative inorganic nickel salts are nickel halides such as nickel chloride, nickel bromide and nickel iodide, nickel carbonate, nickel chlorate, and nickel nitrate. Illustrative organic divalent nickel salts are nickel salts of carboxylic acids such as nickel alkanoates of up to 10 carbon atoms, preferably of up to 6 carbon atoms, e.g., nickel formate, nickel acetate, nickel propionate, nickel hexanoate and the like; nickel oxalate, nickel benzoate and nickel naphthenate. Other suitable organic salts include nickel benzenesulfonate, nickel citrate, nickel dimethylglyoxime and nickel acetylacetonate. Nickel halides, especially nickel chloride, and nickel alkanoates, especially nickel acetate, in part because of their availability at low cost and solubility in diol solvents, are preferred nickel salts.

As a general matter, any boron hydride salt reducing agent of reasonable purity can be suitably employed to prepare the stable nickel complex catalyst precursor or oligomerization catalysts of the referenced disclosures. Specific examples include alkali metal borohydrides such as sodium borohydrides, potassium borohydride and lithium borohydride; alkali metal alkoxyborohydrides wherein each alkoxy has 1-4 carbon atoms, such as sodium trimethoxyborohydride and potassium tripropoxyborohydride and tetraalkylammonium borohydrides wherein each alkyl has 1-4 carbon atoms, such as tetraethylammonium borohydride. Largely because of commercial availability, alkali metal borohydrides are preferred and especially preferred is sodium borohydride.

The diol solvent used as the oligomerization reaction solvent and to prepare the stable nickel complex catalyst precursor and the oligomerization catalysts is an aliphatic diol of 2 to 7 carbon atoms. While different aliphatic diol solvents may be employed in the preparation of the catalyst precursor and/or oligomerization catalysts and in the oligomerization reaction itself, it is preferable to use the same diol solvent in both operations. In this regard, suitable aliphatic diols include vicinal alkane diols such as ethylene glycol, propylene glycol, 2-methyl-1,2-propane-diol, 1,2-butanediol and 2,3-butanediol and alpha-omega alkane diols such as 1,4-butanediol, 1,5-pentanediol, 1,6-hexanediol and 1,7-heptandiol. Alpha-omega alkane diols of 4 to 6 carbon atoms are preferred solvents with 1,4-butanediol being particularly preferred. In some cases it may be desirable to employ mixtures of the above-mentioned alkane diols as the solvent source for the catalyst precursor preparation and/or the oligomerization reaction.

The base employed in combination with the nickle salt, the boron hydride transfer agent and ethylene to make up the stable nickel complex catalyst precursor of the most preferred mode, i.e., that described in the aforementioned U.S. patent application Ser. No. 116,687, is suitably an alkali metal or alkaline earth metal hydroxide. In this regard, it is preferable to employ alkali metal hydroxides with sodium or potassium hydroxide being most preferred. Typically, the base is used as about a 0.1 to 3.0 M solution in water.

The oligomerization reaction can be carried out in a batch or continuous manner and is suitably conducted at temperatures in the range from about 25° C. to 150° C., but preferably from about 70° C. to 100° C. The pressure must be at least sufficient to maintain the reaction mixture substantially in liquid phase although excess ethylene will be present in vapor phase. Pressures in the range from about 300 psig to 5,000 psig may be employed. Other than for maintaining the liquid phase condition of the system, the total pressure is less significant than the partial pressure of ethylene, which is a primary factor in maintaining the desired ethylene concentration in the solvent phase where the oligomerization reaction takes place. In the preferred system, the ethylene partial pressure is suitably in the range from about 400 psig to 2,500 psig and preferably between about 1,000 and 2,500 psig. The concentration of catalyst, calculated as nickel metal, in the solvent phase is at least about 0.001 molar and suitably from about 0.002 to 0.004 molar.

The molar ratios of catalyst components employed to make up the nickel complex catalysts in the oligomerization reaction zone will be somewhat dependent on whether the entire catalyst composition is preformed and added to the reaction zone as a single component or if the stable nickel complex catalyst precursor is preformed according to the most preferred mode and added separately from the bidentate ligand to the oligomerization reaction zone. In the case where all of the catalyst components are mixed together and added as a single preformed composition to the reaction zone, the molar ratio of nickel to bidentate ligand is desirably at least 1:1 with ratios in the range of 1:1 to 5:1 being suitable and molar ratios in the range of about 1.5:1 to 3:1 being preferred. Most preferred in this case are nickel salt to ligand molar ratios of about 2:1. The stable nickel complex catalyst precursor case employs similar broad and preferred ranges for the molar ratio of the nickel salt to bidentate ligand but in the most preferred case the nickel to bidentate ligand molar ratio is reduced to 1.5:1.0 in view of the higher catalyst activity obtained. In cases where the catalyst composition is preformed by adding all of the catalyst components together in the diol solvent and in the presence of ethylene, the boron hydride to nickel molar ratio suitably ranges between about 1:1 to about 15:1 with ratios in the range of 1:1 to 10:1 being preferred. In these cases a boron hydride to nickel salt molar ratio of about 2:1 is most preferred. In the case where the stable nickel salt catalyst precursor is employed, the molar ratio of nickel to boron hydride used in the precursor preparation suitably ranges between about 0.2:1.0 to about 2.0:1.0 with molar ratios in the range of about 0.5:1.0 to 1.0:1.0 being preferred. In the catalyst precursor case, the molar ratio of nickel to the base component used to prepare the stable catalyst precursor is suitably in the range of about 0.33:1.0 to about 10.0:1.0 with ratios in the range of about 0.5:1.0 to 4.0:1.0 being preferred. In both cases, the catalyst composition and the stable catalyst precursor composition must be prepared in the presence of ethylene, suitably sufficient ethylene, pressure to saturate the diol solution with ethylene. Typically, the ethylene pressures employed may be in the range of from 10 to 5000 psig or higher with pressures in the range of from about 500 to about 2000 psig being preferred.

The reaction product from the oligomerization reaction zone contains three phases: (1) a liquid diol solvent phase in which the nickel complex catalyst is dissolved (2) a liquid hydrocarbon phase made up predominantly of ethylene oligomers and including dissolved ethylene and minor amounts of solvent and nickel complex catalyst and (3) gaseous ethylene. The improvement according to the invention can be used to advantage in any recovery system wherein the liquid solvent phase (1) is phase separated from the hydrocarbon phase and gaseous ethylene and all or a portion of the solvent in the separated phase is recovered in purified form from the contained catalyst by distillation or fractionation at elevated temperatures. The improvement according to the invention, i.e., the addition of an alkali metal hydroxide to the distillation zone, effectively inhibits the tendency for the diol solvent to form oxygenated degradation products at elevated temperatures in the presence of the catalyst. As noted above, the diol solvent degradation products are typically oxygenated materials formed by loss of hydrogen and/or water from the solvent molecule. With the preferred alpha, omega-alkanediol reaction solvents, the predominating degradation products are acetals and hemiacetals. For example, 1,4-butanediol, the most preferred diol reaction solvent, typically forms a variety of cyclic acetals and hemiacetals including 2-hydroxytetrahydrofuran, 2,2'-bis(tetrahydrofuryl)ether, 2-(4-hydroxybutyloxy)tetrahydrofuran and 1,4-bis(2-tetrahydrofuryloxy)butane as the principle degradation products. With the preferred ligands of the invention, i.e., dehydrocarbylphosphinobenzoic acid and dicyclohexyl phosphinopropionic acid, an additional advantage is obtained with the improvement according to the invention in that the alkali metal hydroxide placed into contact with the catalyst-containing solvent in the distillation zone apparently reacts with minor amounts of free carboxylic acid (benzoic acid and propionic acid) which are formed from the ligand during the oligomerization reaction and subsequent processing steps. This reaction converts the free carboxylic acid impurities into nonvolatile salts which are then removed with the spent catalyst bottoms product on distillation. Since a significant concentration of these carboxylic acid impurities could adversely affect the performance of the oligomerization catalyst, their removal from the recovered solvent allows the recovered solvent to be recycled to the oligomerization reaction zone without ay risk of oligomerization catalyst contamination. Further, the improvement according to the invention serves as a convenient means of avoiding build-up of these free carboxylic acid impurities in cases where the recovered diol solvent is reused in the process.

The improvement according to the invention is applicable to diol solvent recovery operations carried out on a batch or continuous basis, i.e., batch or continuous distillation of the catalyst-containing diol solvent phase. It is particularly suited for distillations carried out at a temperature above 135° C., since formation of the oxygenated degradation products from the diol solvent becomes most significant at these higher temperatures. To affect the improvement according to the invention in either batch or continuous operations, the alkali metal hydroxide is suitably added as a concentrated aqueous solution either in admixture with the catalyst-containing solvent stream charged to the solvent recovery zone or as a separate stream into the liquid heel in the solvent recovery zone, i.e., distillation or flash vessel. In this manner, the alkali metal hydroxide contacts and remains in contact with the diol solvent which is subject to the highest temperatures in the solvent recovery zone. The quantity of alkali metal hydroxide required to inhibit oxygenated diol solvent degradation product formation is small as compared to the volume of catalyst-contaminated diol solvent being treated. Typically, the quantity of alkali metal hydroxide employed is based on the concentration of catalyst in the diol solvent treated and suitable results may be obtained using from about 10 to about 0.5 moles of alkali metal hydroxide per gram atom (g-atom) of nickel metal in the catalyst-containing solvent being treated. Preferably, from 3 to 1 moles of alkali metal per mole of nickel metal are employed with best results being obtained when about 2 moles of alkali metal hydroxide are added to the solvent recovery zone for every g-atom of nickel metal in the catalyst-containing diol solvent charged to the recovery zone.

The alkali metal hydroxide employed in the improvement according to the invention is suitably a hydroxide of alkali metals having atomic weights of from 11 to 132 or mixtures thereof, i.e., sodium, potassium, rubidium and cesium hydroxides. Preferably, the alkali metal hydroxide used is sodium hydroxide or potassium hydroxide with potassium hydroxide being most preferred. As noted above, this alkali metal hydroxide is most conveniently used in the form of a concentrated aqueous solution, preferably a 3 to 12 molar aqueous solution.

In its preferred application, the improvement according to the invention is applied to the oligomerization reaction system described in the aforementioned U.S. Pat. No. 4,020,121 as modified by the subsequent U.S. patent application disclosures referenced above. In the solvent recovery and recycle system described in this U.S. patent a minor portion 2 to 4 percent of the catalyst-containing diol reaction solvent which has been phase separated from the liquid hydrocarbon oligomer product is passed continuously to a distillation or rectification column where purified solvent is taken as a side stream with light end impurities taken overhead and spent catalyst removed as a bottom product. In typical operations, this distillation is affected by charging the catalyst-containing solvent stream to the bottom portion of a column operated at a bottoms temperature of from about 135° C. to about 165° C. and a pressure of from about 20 mm to about 40 mm. The alkali metal hydroxide, preferably sodium or potassium hydroxide, is added on a continuous basis as a 3 to 12 molar aqueous solution to the bottom of the distillation column either by means of a mixing "T" in the diol solvent inlet line or a separate inlet line into the liquid heel in the bottom of the column. By adding the alkali metal hydroxide in this manner at about a 2:1 mole ratio of alkali metal hydroxide to nickel metal in the catalyst-containing solvent stream it is possible to achieve a substantial reduction, i.e., greater than 90% w in extended thermal aging, in the make of oxygenated diol solvent degradation products which would otherwise be encountered in this solvent recovery step. The recovered diol solvent, i.e., the purified solvent taken as a side draw stream in the fractionation column, can then be reused in the oligomerization process scheme as indicated in the aforementioned U.S. Pat. No. 4,020,121. That is, it can be used in preparation of the stable nickel complex catalyst precursor, the oligomerization catalyst itself or in the hydrocarbon product scrubbing step of the recovery process described therein.

The effectiveness of the alkali metal hydroxide treatment in inhibiting the formation of oxygenated diol solvent degradation products on thermal treatment of a diol solvent containing a nickel complex oligomerization catalyst is demonstrated in the following illustrative embodiment.

ILLUSTRATIVE EMBODIMENT

To demonstrate the improvement according to the invention, an aliphatic diol (1,4-butanediol) containing a nickel complex oligomerization catalyst was thermally aged at 135° and then at 165° C. with an without added alkali metal hydroxide (potassium hydroxide) and the concentrations of the major oxygenated diol degradation products which form with time during the thermal treatment were measured. The diol degradation products measured at periodic intervals during the test included 2-(4-hydroxybutyloxy) tetrahydrofuran, and 2-hydroxytetrahydrofuran. The catalyst-containing diol solvent used in these tests was obtained from the liquid-liquid phase separation step of an oligomer and solvent recovery process carried out according to the teachings of U.S. Pat. No. 4,020,121 on the reaction product of a continuous ethylene oligomerization in 1,4-butanediol reaction solvent using a nickel complex catalyst prepared by reacting diphenylphosphinobenzoic acid with nickel chloride hexahydrate and sodium borohydride in the presence of ethylene and 1,4-butanediol. As employed in the thermal aging tests, this catalyst-containing diol solvent feedstock is typical of that which would be charged to the solvent recovery zone in the process of U.S. Pat. No. 4,020,121.

The thermal aging tests were conducted by charging 1560 grams of catalyst-containing diol solvent to 3-necked 2-liter flasks equipped with a condenser, thermometer, boiling chips and a nitrogen blanket. After adding the diol solvent feedstock, the temperature was raised to an initial 135° C.±3° C. and maintained for 144 hours by means of heating mantles. Subsequently, the temperature in the flasks was increased to 165° C.±3° C. and held for an additional 200+ hours with samples being taken at periodic intervals throughout the tests to determine the concentration level of the various oxygeneated diol solvent degradation products mentioned above. For comparison and to show the effects of nickel complex catalyst on the rate of diol solvent degradation a third thermal aging test was conducted under similar conditions (nitrogen atmosphere, etc.) with pure 1,4-butanediol feedstock. The samples withdrawn at periodic intervals from each of the test flasks were analyzed for 1,4-butanediol and degradation product content by gas-liquid chromatography. The results of the tests including further details of the test conditions are given in the Table below.

| Sample Tested | Hours | Temp. °C. | 1,4-butane-diol | Degradation Product A[2] | B[3] |
|---|---|---|---|---|---|
| 1,4-Butanediol containing catalyst | 144 | 135 | 99.23 | 0.20 | Trace |
| | 24 | 165 | 96.80 | 0.97 | 0.04 |
| | 50 | 165 | 96.75 | 1.36 | 0.02 |
| | 144 | 165 | 94.63 | 2.99 | 0.04 |
| | 168 | 165 | 94.17 | 3.52 | 0.04 |
| | 213 | 165 | 92.34 | 4.65 | 0.05 |
| 1,4-Butanediol containing catalyst (KOH treated)[1] | 144 | 135 | 99.25 | 0 | Trace |
| | 64 | 165 | 97.94 | Trace | 0.01 |
| | 168 | 165 | 97.77 | 0.20 | 0.02 |
| | 207.5 | 165 | 97.72 | 0.28 | 0.02 |
| Pure 1,4-butanediol | 144 | 135 | 99.6 | 0 | Trace |
| | 24 | 165 | 98.61 | Trace | 0.01 |
| | 68 | 165 | 98.07 | 0.05 | Trace |
| | 144 | 165 | 98.41 | 0.08 | 0.01 |
| | 168 | 165 | 97.87 | 0.11 | 0.01 |
| | 211 | 165 | 98.28 | 0.12 | 0.01 |

[1]Catalyst-containing solvent mixed with potassium hydroxide in a quantity to provide 2 moles of KOH per mole of contained nickel prior to heat treatment.
[2]2-(4-Hydroxybutyloxy)tetrahydrofuran
[3]2-Hydroxytetrahydrofuran

What is claimed is:

1. In the process for the recovery of an aliphatic diol reaction solvent in the processing scheme wherein ethylene is oligomerized at elevated temperature and pressure by contact with a solution of a nickel complex catalyst in an aliphatic diol solvent to afford a reaction product made up of (a) a liquid solvent phase containing dissolved catalyst, (b) a liquid hydrocarbon phase comprising ethylene oligomers containing dissolved ethylene, catalyst and diol solvent and (c) gaseous ethylene, said reaction product being passed to a series of phase separation zones whereby gaseous ethylene and a substantial portion of the diol reaction solvent containing dissolved catalyst are separated and recycled to the oligomerization reaction zone with a minor portion of the separated catalyst-containing reaction solvent being passed to a fractionation zone for removal of light ends and spent catalyst, prior to its recycle to the oligomerization process; the improvement which comprises, contacting the catalyst-containing, diol reaction solvent in the fractionation zone with a minor amount of an alkali metal hydroxide thereby minimizing the formation of oxygenated degradation products from the diol solvent during fractionation.

2. The process according to claim 1, wherein the aliphatic diol solvent employed is an aliphatic diol of 2 to 7 carbon atoms.

3. The process according to claim 2 wherein the aliphatic diol solvent is a vicinal alkane diol or an alpha-omega alkane diol.

4. The process according to claim 3, wherein the alkali metal hydroxide is sodium hydroxide or potassium hydroxide.

5. The process according to claim 4, wherein the fractionation is carried out at a temperature above about 135° C.

6. The process according to claim 5, wherein the solvent in the fractionation zone is contacted with from about 10 to about 0.5 moles of alkali metal hydroxide per g-atom of nickel metal in the catalyst-containing solvent being fractionated.

7. The process according to claim 6 wherein about 2 moles of alkali metal hydroxide are added to the fractionation zone for every g-atom of nickel metal in the catalyst-containing diol solvent charged to the fractionation zone.

8. The process according to claim 7, wherein the alkali metal hydroxide is potassium hydroxide.

* * * * *